Figure 1:
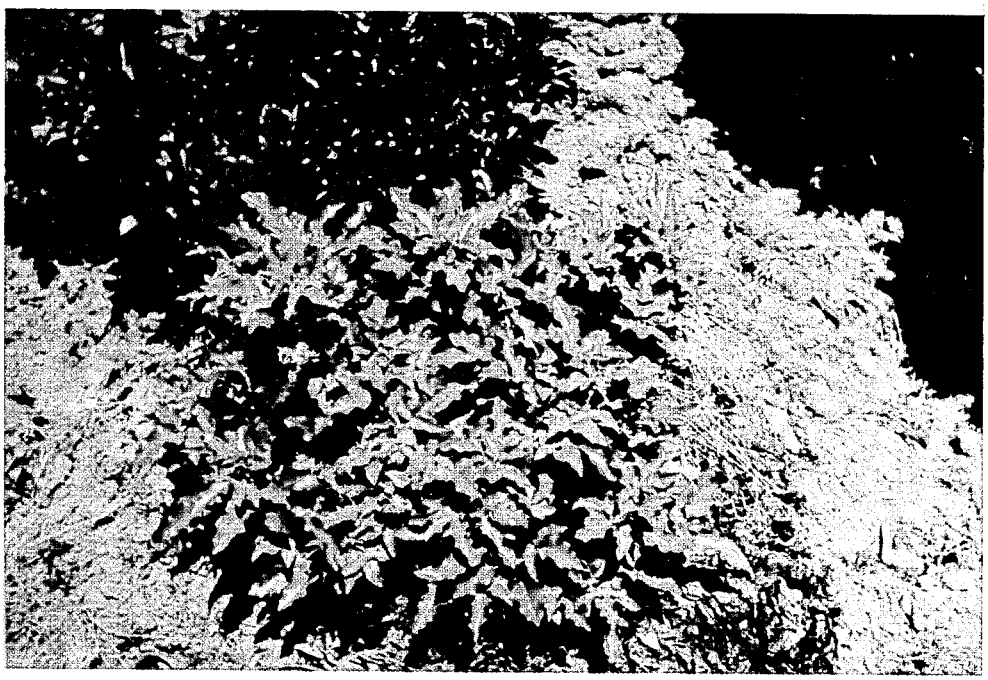

OREGON GRAPE HOLLY SHRUB

Filed Feb. 6, 1964 2 Sheets-Sheet 1

INVENTOR
CHARLES SZERSZEN
BY Philip D. Golrick
ATTORNEY

OREGON GRAPE HOLLY SHRUB

Filed Feb. 6, 1964 2 Sheets-Sheet 2

INVENTOR
CHARLES SZERSZEN
BY Philip D. Golrick
ATTORNEY

United States Patent Office

Plant Pat. 2,544

Patented July 13, 1965

2,544

OREGON GRAPE HOLLY SHRUB

Charles Szerszen, 27819 Center Ridge Road, Westlake, Ohio

Filed Feb. 6, 1964, Ser. No. 343,172
1 Claim. (Plt.—54)

The present invention or discovery relates to a new and distinct variety of Oregon grape holly shrub (*Mahonia aquifolium*).

The Oregon grape holly shrub species in its new growth or wood first evidences tender shoots which change from a paler to darker green, exhibiting varying amounts of red pigment in the process, but in any event deepening to a late fall color of wine red.

The instant variety in the new growth goes through a color change from an initial yellow-greenish color, which with time and growth deepens through bright orange bronze and then to scarlet, beginning at the leaf edges and moving inwardly toward the stems until an entirely scarlet leaf results. Thus at one stage a spectrum of colors is present in individual leaves ranging from yellow-greenish at the stems through bright orange to a scarlet at the edges with no sharp demarcations, but rather a continual gradation from one extreme through the intermediate colors to the other extreme of scarlet or red at the edges where the leaf is not heavily shaded. In the latter case, heavily shaded areas may develop only to partial coloration. With continued growth the scarlet then advances inward from the edges, so that finally when the new growth has halted and is about to begin hardening, an even scarlet has been attained. In the same growth, the first leaves are usually more advanced in the cycle of color change than later leaves. With hardening, the scarlet deepens to a dark red, at times progressing from the edges of the leaves inwardly, at times the deepening of the color occurring simultaneously throughout the leaf.

Thereafter, when new growth appears, which also goes through the same gradation and change in color, the older, now dark red growth lower on the shrub in greatest part turns green under the shading effect of higher new growth except that some of the dark red may remain in leaf areas strongly exposed to sunlight, as at edges of leaves, which areas attain dark green only after a much longer period of time.

This cycle of color change with growth from the first emergence of new foiliage through the full scarlet and darker red to the incipient turning to dark green involves approximately five to six weeks as the growing cycle. The first cycle of color transition begins after the flowering period, in May for northern Ohio; the dark red color being attained about the middle of June. New summer growth follows the same color cycle.

Moreover, the foliage of this new variety has a consistently beautiful glossy aspect and is markedly spinous; and the parent tree is bushy and compact in growth.

This remarkable spectrum of color and color change in the new growth is an outstanding characteristic rendering the shrub particularly of interest for ornamental plantings.

The new variety seems quite hardy, for thus far the propagules appear to withstand winter weather in northern Ohio, as low as 25° F. below zero, better than most specimens of the species, with no winter burning, winter kill or sunburn by comparison with the species.

The parent was originally selected from a group of about 500 seedlings of the Oregon grape holly shrub planted in the applicant's nursery at Westlake, Ohio, because of its glossier foliage and the character of the serration of the leaves, and proved to be the only one of the entire group exhibiting the color and color change characteristics in the foliage as above described.

The new variety has been propagated asexually by rooting cuttings of the wood from the parent specimen, and the above described color characteristics of the new variety have been found in all the propagules.

Figure 2:
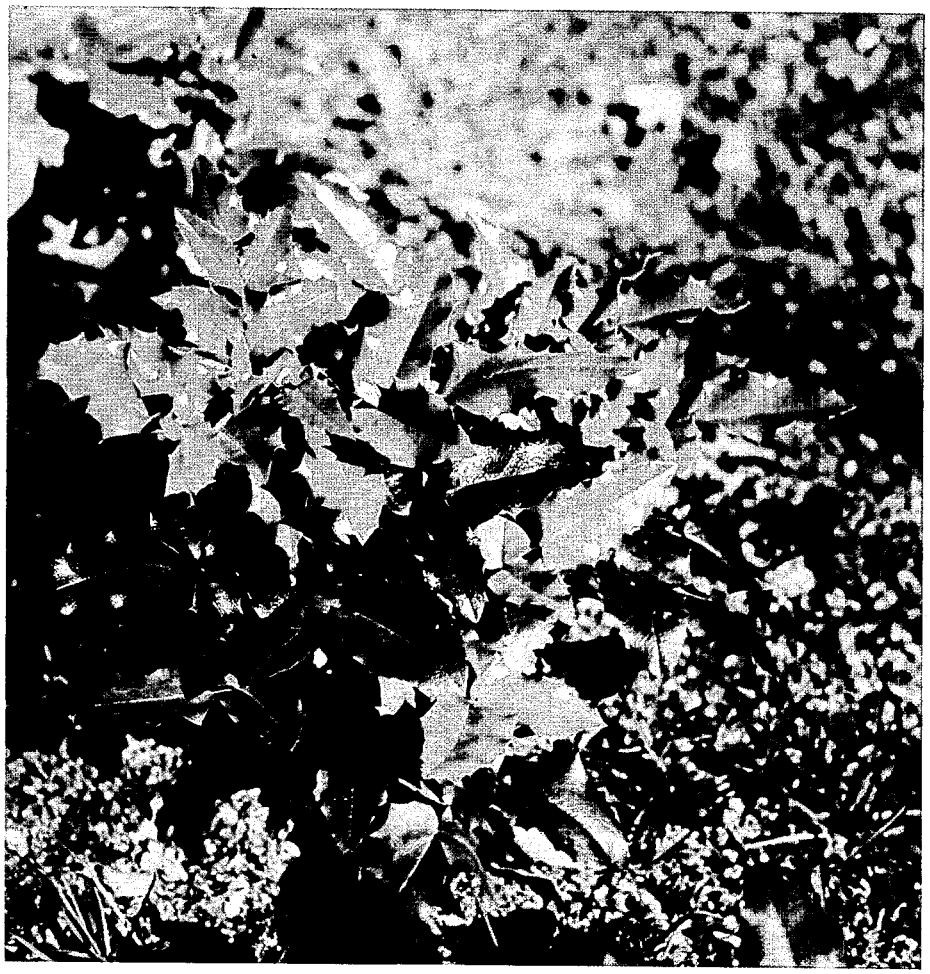

In the drawings,

FIG. 1 is a specimen of the new variety of shrub with new growth in the color transition stage, wherein may be seen the range of color which occurs throughout the shrub as a whole, from leaf to leaf and within individual leaves; and FIG. 2 is a close up view of a specimen of the new variety in which the full scarlet color has appeared throughout most of the leaves of the new growth with a few still having a gradation of color, and showing clearly the leaf form.

The new variety has the following characteristics in common with those of the species as set forth in Rehder, Manual of Cultivated Trees and Shrubs (2 ed.), page 224:

Height of shrub: Grows to at least one meter.

Leaflets: 5–9, ovate to oblong-ovate, 3.5–8 cm. long, rounded or truncate at base, sinuately spiny-dentate, lustrous dark green above, rarely dull, without distinct papillae below, stiff and leathery.

Petioles: Slender, 2–5 cm. long.

Racemes: Fascicled, erect, 5–8 cm. long, at end of the branches.

Fruit: Bluish black, bloomy, about 8 mm. across.

Flowers: Bright yellow flowers in spring.

As determined with, and in terms of the designations used in, "Nickerson Color Fan, Maximum Chroma, 40 Hues," published by Munsell Color Company, 1957, the color ranges are:

For the stated initial yellow-greenish color, about 7.5YR 6/7;

For the bright orange stage between 2.5YR 6/12–5YR 6/11 and 7.5YR 8/8–7/11;

For the scarlet stage, 7.5R 4/11–10R 4/9;

For the dark red stage, between 5R 3/7–7.5R 3/6 and 5R 4/12–7.5R 4/11.

It is to be understood, however, that as there is a gradation of color in individual leaves without sharp demarcation of color areas, so also there the term "stage" as above used does not represent a sharp change in behaviour of color change, but rather an attempt to describe an overall impression on the observer.

I claim:

A new and distinct variety of Oregon grape holly shrub (*Mahonia aquifolium*), characterized by the range of colors and color-change displayed in the new growth, changing from an initial yellow-greenish color in individual leaves through bright orange to scarlet as the growth continues, the color change usually progressing inwardly from the edge of the individual leaf to the stem, until a bright scarlet is attained throughout the leaf, the scarlet foliage as the new growth hardens becoming a substantially solid deep red colored leaf before turning to a dark green in the mature growth with at times some red remaining for a much longer time in parts exposed to strong sunlight.

No references cited.

ABRAHAM G. STONE, *Primary Examiner.*